(12) United States Patent
Franz et al.

(10) Patent No.: US 11,019,983 B2
(45) Date of Patent: Jun. 1, 2021

(54) FLEXIBLE STEM INSTRUMENT WITH A SPINDLE DRIVE ACTUATED LINKAGE

(71) Applicant: Scholly Fiberoptic GmbH, Denzlingen (DE)

(72) Inventors: Marcus Franz, Bad Krozingen-Biengen (DE); Matthias Kratschmer, Freiburg (DE)

(73) Assignee: Schölly Fiberoptic GmbH, Denzlingen (DE)

( * ) Notice: Subject to any disclaimer, the term of this patent is extended or adjusted under 35 U.S.C. 154(b) by 448 days.

(21) Appl. No.: 15/767,238

(22) PCT Filed: Dec. 1, 2016

(86) PCT No.: PCT/EP2016/002031
§ 371 (c)(1),
(2) Date: Apr. 10, 2018

(87) PCT Pub. No.: WO2017/097405
PCT Pub. Date: Jun. 15, 2017

(65) Prior Publication Data
US 2019/0069762 A1 Mar. 7, 2019

(30) Foreign Application Priority Data
Dec. 8, 2015 (DE) .......................... 102015015772.8

(51) Int. Cl.
*A61B 1/00* (2006.01)
*A61B 1/018* (2006.01)
*G02B 23/24* (2006.01)
*A61B 1/008* (2006.01)
*A61B 1/06* (2006.01)

(52) U.S. Cl.
CPC .......... *A61B 1/00098* (2013.01); *A61B 1/008* (2013.01); *A61B 1/00087* (2013.01); *A61B 1/00096* (2013.01); *A61B 1/00133* (2013.01); *A61B 1/06* (2013.01); *G02B 23/2476* (2013.01); *A61B 1/00066* (2013.01);
(Continued)

(58) Field of Classification Search
CPC ............ A61B 1/00098; A61B 1/00087; A61B 1/0014; A61B 1/00133; A61B 1/018; A61B 1/0615; A61B 2017/00296; A61B 2017/003; A61B 2017/00314; A61B 2017/0034; G02B 23/2476
See application file for complete search history.

(56) References Cited

U.S. PATENT DOCUMENTS 3,496,930 A * 2/1970 Wappler ................. A61B 1/307
600/135
4,881,524 A * 11/1989 Boebel ............... A61B 1/00098
600/108
(Continued)

FOREIGN PATENT DOCUMENTS

JP 2014128465 7/2014

*Primary Examiner* — John P Leubecker
(74) *Attorney, Agent, or Firm* — Volpe Koenig

(57) ABSTRACT

An instrument (1), in which a main part (6) and a folding part (7) that can be extended therefrom are formed at the distal end (3) of a flexible shaft (2). The folding part (7) can be extended via a linkage (8) that can be adjusted by a spindle drive (9), and the spindle drive (9) can be driven from a proximal end (4) of the flexible shaft (2) via a flexible shaft (12).

17 Claims, 4 Drawing Sheets

(52) U.S. Cl.
CPC ........... *A61B 1/00177* (2013.01); *A61B 1/018* (2013.01); *A61B 1/0615* (2013.01)

(56) References Cited

U.S. PATENT DOCUMENTS

| | | | | |
|---|---|---|---|---|
| 5,258,004 | A * | 11/1993 | Bales | A61B 17/320016 606/205 |
| 5,308,358 | A * | 5/1994 | Bond | A61B 17/29 606/170 |
| 5,318,589 | A * | 6/1994 | Lichtman | A61B 17/29 600/564 |
| 5,573,493 | A * | 11/1996 | Sauer | A61B 1/00101 600/121 |
| 5,649,955 | A * | 7/1997 | Hashimoto | A61B 17/29 600/562 |
| 5,964,780 | A * | 10/1999 | Balazs | A61B 17/29 606/205 |
| 8,602,980 | B2 * | 12/2013 | Bassan | A61B 1/00183 600/173 |
| 8,652,150 | B2 * | 2/2014 | Swain | A61B 17/0469 606/139 |
| 9,333,001 | B2 * | 5/2016 | Stokes | A61B 17/29 |
| 9,468,426 | B2 * | 10/2016 | Conlon | A61B 17/29 |
| 2001/0018550 | A1 * | 8/2001 | Boebel | A61B 1/018 600/107 |
| 2005/0015113 | A1 | 1/2005 | Baptiste et al. | |
| 2005/0234296 | A1 * | 10/2005 | Saadat | A61B 1/00183 600/129 |
| 2008/0112751 | A1 * | 5/2008 | Sheets | A61B 17/00491 401/134 |
| 2010/0229669 | A1 * | 9/2010 | Kim | B25J 9/106 74/490.01 |
| 2011/0152610 | A1 | 6/2011 | Trusty et al. | |
| 2011/0184459 | A1 * | 7/2011 | Malkowski | A61B 17/2909 606/206 |
| 2012/0041264 | A1 * | 2/2012 | Blase | A61B 1/126 600/121 |
| 2015/0031947 | A1 | 1/2015 | Kudo et al. | |
| 2015/0119918 | A1 | 4/2015 | Blase et al. | |
| 2015/0257629 | A1 | 9/2015 | Shahinian | |

* cited by examiner

FLEXIBLE STEM INSTRUMENT WITH A SPINDLE DRIVE ACTUATED LINKAGE

BACKGROUND

The invention relates to an instrument having a flexible stem which has a distal end and a proximal end, wherein a handling element is disposed on the proximal end, and the main part is configured on the distal end, wherein a fold-out part is disposed so as to be adjustable by way of a linkage between a first position, disposed on the main part, and a second position which in relation to a profile direction of the stem is laterally spaced apart from the main part.

The invention furthermore relates to a use of an instrument of this type for machining, in particular repairing, a component that is disposed within a cavity.

Instruments of this type are known and are used, for example, as medical instrument systems or endoscopes so as to treat various tissues in a body orifice while the tissue and/or the treatment are/is observed.

It has become commonplace herein for the linkage mentioned to be activated by way of flexible traction element from the proximal end of the flexible stem. A changeover between a fully folded-in and a fully folded-out position of the fold-out part is thus achievable.

SUMMARY

The invention is based on the object of improving the performance characteristics of an instrument of the type mentioned at the outset.

In order for this object to be achieved according to the invention, one or more of the features of the invention are provided in an instrument. In particular it is thus proposed according to the invention in the case of an instrument of the type mentioned at the outset in order for the object to be achieved that a spindle drive by way of which the linkage is activatable is configured, and that a threaded part of the spindle drive is drivable by way of a flexible shaft that is routed along the stem. The invention as an alternative to the known activation by way of Bowden controls or similar traction elements, thus provides an activation of the linkage from the proximal end of the flexible stem, by way of a flexible shaft and of a spindle drive. This has the advantage that impediments to the activation capability in the case of a heavily curved profile of the flexible stem are minimizable or even entirely avoidable. It is moreover possible for intermediate positions between a fully folded-in first position, and a fully folded-out second position to be actuated in a defined manner with the invention. The threaded part is preferably a spindle of the spindle drive, said spindle running in a spindle nut that is disposed on the linkage.

In the case of one design embodiment of the invention it can be provided that the flexible shaft is disposed in a guide duct in the flexible stem. An impediment to the rotatability of the flexible shaft for actuating the spindle drive is thus avoidable even in tight or contorted access routes to a cavity. It is particularly favorable herein for an available internal diameter of the guide duct to be chosen to be larger than an external diameter of the flexible shaft in such a manner that the flexible shaft is disposable in the guide duct so as to be spaced apart from the latter on all sides. This can be achieved, for example, in that the available internal diameter of the guide duct is larger than the external diameter.

The flexible shaft is preferably configured as a solid shaft. This enables a particularly simple production of the flexible shaft even in the case of very small external diameters of the shaft.

In the case of one design embodiment of the invention it can be provided that an operation duct that ends on the fold-out part is configured along the stem. It is advantageous herein for a cavity into which the instrument is introduced to be accessible and/or machinable at a location that is spaced apart from the main part. This can be used, for example, for introducing an additional instrument and/or for introducing consumable material by way of the fold-out part.

It is particularly favorable herein for the operation duct to be configured so as to be flexible at least in a portion that lies between the stem and the fold-out part. In this way, the operation duct can permit a conjoint movement of the distal end thereof when the fold-out part is being folded out. It is particularly favorable herein for the flexible portion to be configured so as to be traction-resistant and/or compression-resistant. It is advantageous herein for a guide of the fold-out part to be reachable during the activation of the linkage by way of the operation duct. This simplifies the requirements set for the linkage in terms of construction.

In the case of one design embodiment of the invention it can be provided that the linkage forms a toggle lever. It is advantageous herein for an activation force which is capable of being provided by way of the spindle drive to be capable of being introduced as a deployment force onto the fold-out part by way of the lever effect of the toggle lever, said deployment force increasing as the distance of the fold-out part from the main part increases. This enables a particularly simple deployment of the fold-out part.

It can be provided herein that the spindle drive engages on a toggle joint of the toggle lever. The deployment force already mentioned can thus be particularly great when the linkage reaches the folded-out position thereof and the fold-out part thus reaches the second position.

Alternatively or additionally, it can be provided herein that a free end of the toggle lever engages on the main part. A further free end of the toggle lever can engage on the fold-out part. In this way, a simple support of the fold-out part on the main part in the second position results. It can be provided herein that the free ends of the toggle lever are articulated on the main part or on the fold-out part, respectively. It is advantageous herein for a defined position of the toggle lever to be achievable.

In the case of one design embodiment of the invention it can be provided that a linkage arm of the linkage by way of a first end engages on the fold-out part and by way of a second end is guided so as to be displaceable on the main part. It is advantageous herein for lateral stabilizing in relation to an adjustment direction of the fold-out part to be achievable. This is favorable in particular when a consumable material, for example a gas, fluid and/or solid material, which is unwound from a feed direction and therefore has a winding profile which wants to bend the operation duct is disposed in an operation duct, for example the operation duct already mentioned. The design embodiment mentioned is advantageously combinable with the configuration of the linkage as a toggle lever. The linkage arm mentioned here, between the first end and the second end thereof, can have a toggle joint, for example the already mentioned toggle joint, of the toggle lever. The linkage arm in the case of one design embodiment can engage on the fold-out part in that said linkage arm is articulated on the fold-out part. It is particularly favorable for the displaceable guiding of the second end on the main part to be achieved by a lateral support, for example in a guide groove.

In the case of one design embodiment of the invention it can be provided that a head part is configured on the fold-out part, wherein an actuation point is configured on the head part. The head part herein can be disposed so as to be movable on the fold-out part. It is advantageous herein for an additional mobility of the fold-out part to be provided, said additional mobility potentially being specified so as to be activatable independently of the spindle drive and/or so as to be movable in a manner coupled to the spindle drive. For example, the actuation point can be connected to the linkage, in order to achieve coupled movement of the head part when the spindle drive is operated. This coupled mobility can be achieved, for example, in that the actuation point is connected to a linkage arm of a toggle lever, for example to the toggle lever already mentioned. The actuation point is preferably connected to a linkage arm of the toggle lever which by way of a toggle joint, for example the toggle joint mentioned, of the toggle lever is connected to the fold-out part in an articulated manner.

In the case of one design embodiment of the invention it can be provided that a connection of the actuation point to the linkage is configured such that the head part in the first position of the fold-out part and in the second position of the fold-out part assumes alignments that are mutually offset. It is advantageous herein for a rotating or pivoting movement, by way of which a relative alignment of the head part in relation to the main part changes, to be capable of being carried out conjointly with the head part while the latter folds out from the first position to the second position. It is thus achievable that the head part is rolled up as the fold-out part is folded in. The precise profile of this movement that is preferably coupled to the spindle drive is capable of being predefined by the positioning of the connection points on the linkage and by the length of the respective connections. For example, it is achievable for the head part in the first position of the fold-out part and in the second position of the fold-out part to assume mutually opposite alignments.

In the case of one design embodiment of the invention it can be provided that the linkage has a further adjustment device by way of which at least a head part, for example the head part already mentioned, of the fold-out part, at least in the second position, is adjustable relative to the main part in the case of a stationary spindle drive. It is advantageous herein for an alignment of the head part to be variable in the case of a folded-out fold-out part.

In the case of one design embodiment of the invention it can be provided that the main part is configured as a rigid part. It is advantageous herein for a stress-capable base for supporting the fold-out part while the latter is being folded out to be achievable. Defined guiding of a folding-out movement is thus also achievable. Alternatively or additionally, it can be provided that the fold-out part is configured as a rigid part. It is advantageous herein for a defined engagement of the linkage on the fold-out part to be achievable.

It is desirable for the rigid parts of the instrument to occupy a construction length that is as small as possible at the distal end in order for the instrument to be able to be introduced in as flexible a manner as possible into a cavity. To this end, it can be provided that the fold-out part in the first position is received in a receptacle of the main part. This, in the first position of the fold-out part, enables an external diameter of the instrument that is as small as possible at the distal end.

Alternatively or additionally, it can be provided that at least one operation and/or observation unit is configured on the main part in a region in which the fold-out part in the first position bears on the main part. It is advantageous herein for an extension of the main part in the profile direction not to be required beyond an extent of the fold-out part. For example, the operation and/or observation unit can be an illumination unit and/or a camera and/or a laser light exit location. An observation by way of a camera, an illumination of a location to be machined, and/or machining of a location to be machined by laser light are/is thus capable of being carried out.

In the case of one design embodiment of the invention it can be provided that a feed installation for a consumable material that is conveyed in an operation duct, for example in the operation duct already mentioned, is configured. This consumable material can be, for example, a gas, fluid and/or a solid material. It is advantageous herein for machining to be capable of being carried out in a cavity in a simple manner by the instrument while using a consumable material.

In the case of one design embodiment of the invention it can be provided that a machining unit is configured on the main part. This machining unit can be, for example, a milling, boring and/or cutting unit. It is advantageous herein for an observation of the use of the machining unit by means of the fold-out part to be achievable when a respective operation and/or observation unit is configured on the fold-out part. Conversely, the machining unit, in particular the milling, boring and/or cutting unit, can be configured on the fold-out part. In this case, an assessment of the machining unit is achievable by way of an operation and/or observation unit on the main part.

In the case of one design embodiment of the invention, operation and/or observation units are configured in each case on the main part and on the fold-out part, for example in order to enable stereoscopic viewing.

In the case of one design embodiment of the invention it can be provided that a laser fiber, thus a fiber optics for laser light, for example, of a laser exit location is fed in the flexible stem on the main part and/or on the fold-out part. It is advantageous herein that the configuration of a laser generator at the distal end can be dispensed with. Rather, the laser generator can be configured at the proximal end, wherein the laser light is coupled in and/or is capable of being coupled in by way of the laser fiber.

In the case of one design embodiment of the invention it can be provided that a camera, for example the camera already mentioned, and/or an illumination unit, for example the illumination unit already mentioned, are/is configured on the fold-out part. Alternatively or additionally, it can be provided that a camera, for example the camera already mentioned, and/or an illumination unit, for example the illumination unit already mentioned, are/is configured on the main part. The invention thus enables the main part and of the fold-out part to be assigned, in a different manner, variable functions, for example for illuminating a machining position from dissimilar directions, and/or for observing a machining position from dissimilar directions, in particular for stereoscopic viewing.

It is particularly favorable for the instrument to be configured as a visualizing instrument. The instrument is preferably configured as an endoscope. The known fields of application of visualizing instruments and of endoscopes are thus opened up to the instrument according to the invention.

One preferred application of the invention lies in the use of an instrument according to the invention, in particular as has been described above and/or according to one of the claims pertaining to an instrument, for repairing a component that is disposed within a cavity. It is provided according to the invention herein that a consumable material, for example the consumable material already mentioned, preferably a gas, fluid and/or a solid material, in particular the gas already mentioned, the fluid already mentioned and/or the solid material already mentioned, by way of which a clearance is filled and/or a material build-up is formed at a defective location of the component, is conveyed by way of the instrument into the cavity. Coating and/or finishing of surfaces are/is also capable of being carried out in this way. Alternatively or additionally, joining methods are also capable of being carried out. Touching up of components that are difficult to access is thus enabled without a removal of the component being required. The component can be an internal wall of a pipe or a movable component and/or a component that is exposed to a particulate flow, for example. The clearance already mentioned can be made, for example, using a machining unit of the instrument or of a further instrument of the same type or at least according to the invention.

BRIEF DESCRIPTION OF THE SEVERAL VIEWS OF THE DRAWINGS

The invention will now be explained in more detail by means of exemplary embodiments, but is not limited to said exemplary embodiments. Further exemplary embodiments are derived from the combination of the features of individual or a plurality of claims with one another and/or with individual or a plurality of features of the exemplary embodiments.

In the figures, in part in a heavily simplified, schematic illustration for explaining the concept of the invention.

DETAILED DESCRIPTION OF THE PREFERRED EMBODIMENTS

Figure 1:
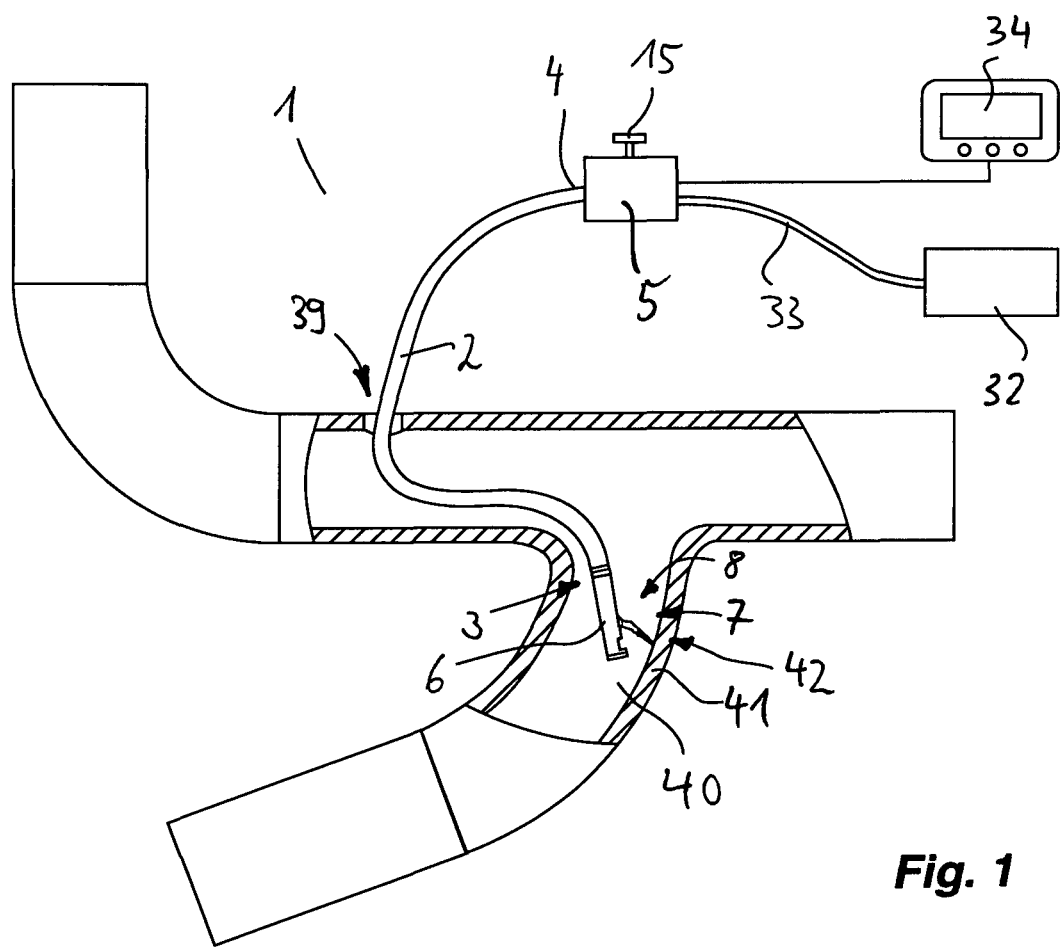
FIG. 1 shows a use of an instrument according to the invention.

FIG. 1 shows an instrument according to the invention that in its entirety is identified by the reference sign 1. The instrument 1 has a flexible stem 2 which runs between a distal end 3 and a proximal end 4. A handling element 5 by way of which the flexible stem 2 is actuatable in a manner known per se is configured at the proximal end 4.

A main part 6 is configured at the distal end 3.

A fold-out part 7, by way of a linkage 8, is fastened to the main part 6 and can be adjusted between a first position in which said fold-out part 7 bears on the main part 6 and a second position in which said fold-out part 7 is deployed from the main part 6 and thus is disposed so as to be spaced apart from the latter.

Figure 2:
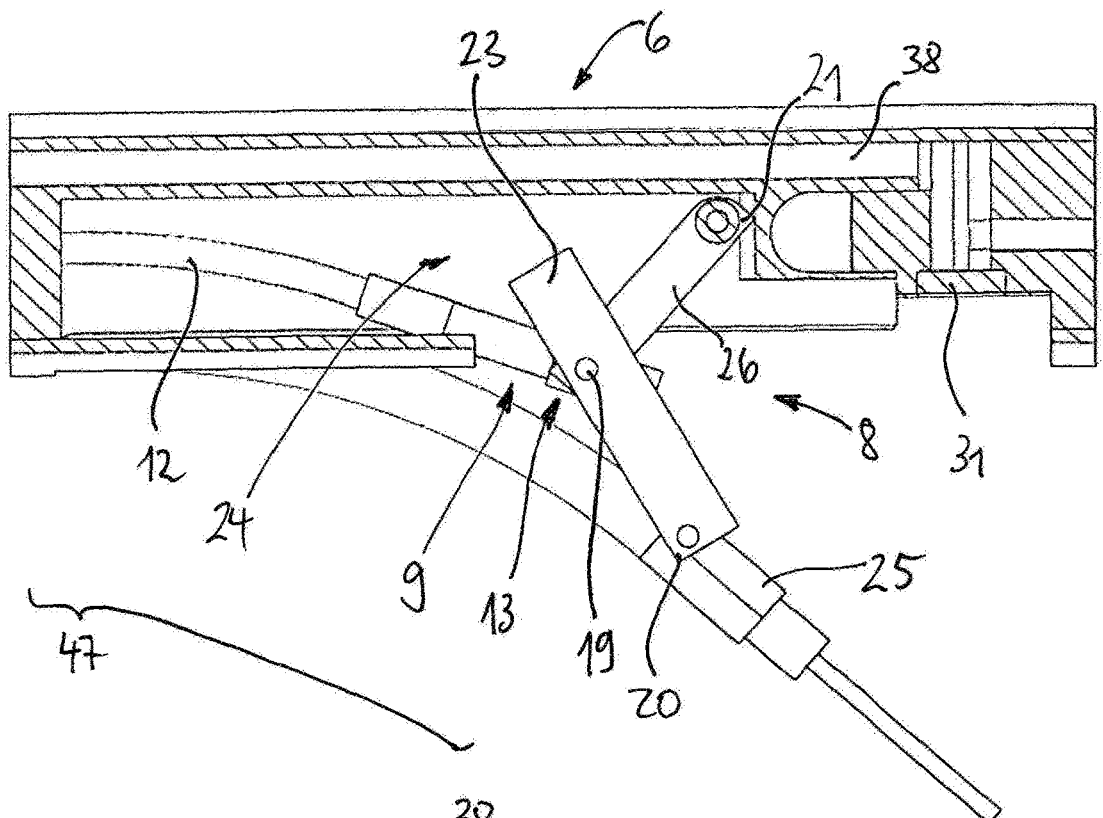
FIG. 2 shows a sectional illustration through the distal end of an instrument according to the invention.

A spindle drive 9 which is illustrated in more detail in FIG. 2 is configured for adjusting the fold-out part 7.

The spindle drive 9 has a threaded part, presently a spindle, which is connected in a rotationally fixed manner to a flexible shaft 12.

The spindle drive 9 has a threaded counterpart 13, presently a spindle nut, which is connected to the linkage 8 and for forming the spindle drive 9 receives the threaded part.

The flexible shaft 12 is routed along the flexible stem 2 toward the handling element 5, and is drivable by way of an adjustment element 15 on the handling element 5. This adjustment element can be operated by hand and/or by motor.

Figure 3:
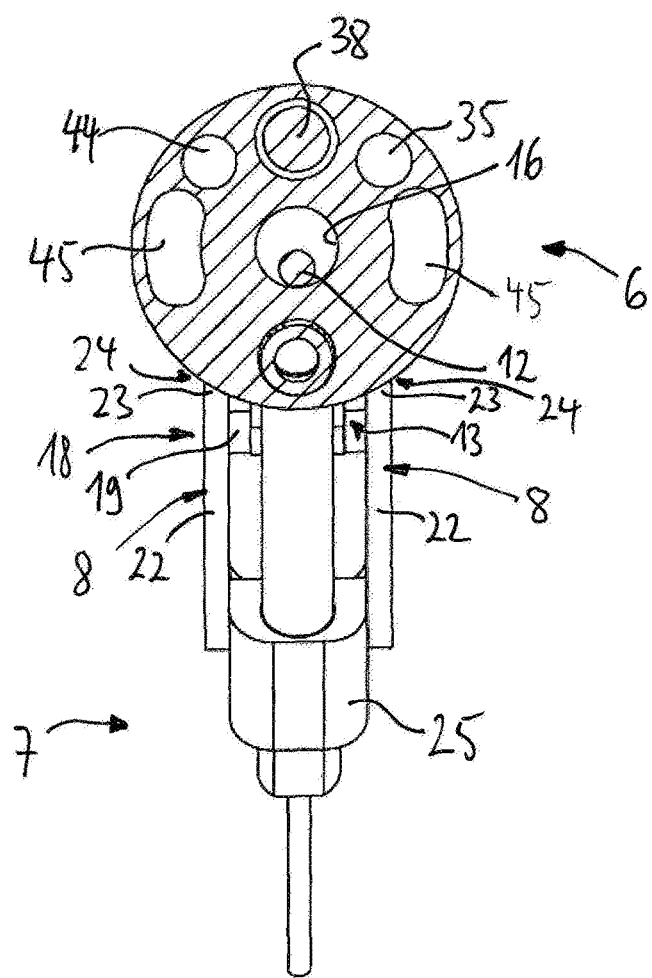
FIG. 3 shows a sectional illustration having a section plane through the distal end of the instrument that runs perpendicularly to the profile direction of the instrument.
Figure 4:
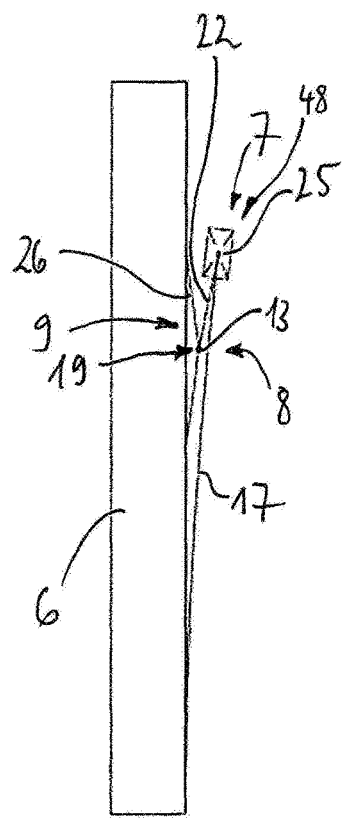
FIG. 4 shows the distal end of an instrument according to the invention, having a folded-in fold-out part in a first position.
Figure 5:
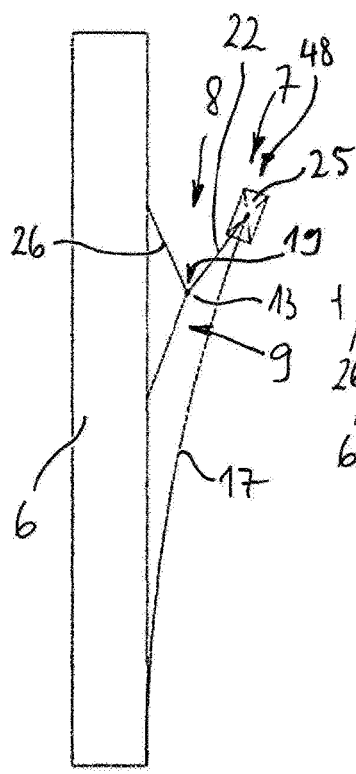
FIG. 5 shows the distal end from FIG. 4, having a partially folded-out fold-out part in an intermediate position.
Figure 6:
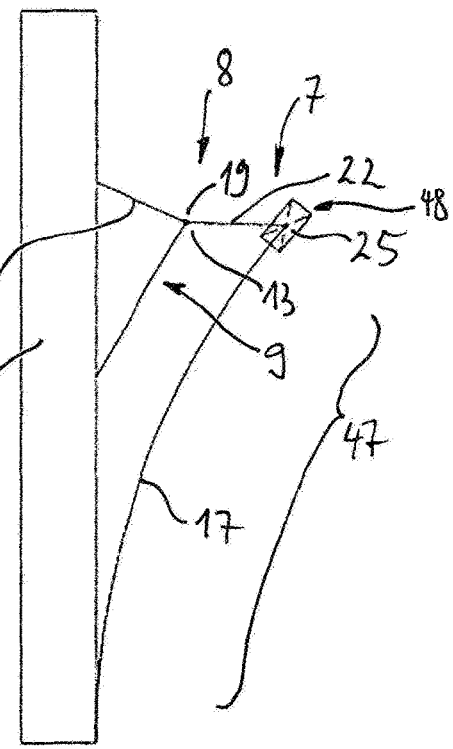
FIG. 6 shows the distal end according to FIG. 4, having a fully folded-out fold-out part in the second position.

The spindle drive 9 by way of the adjustment element 15 is thus drivable from the proximal end 4 of the flexible stem 2. On account thereof, a deployment of the fold-out part 7 from a first, folded-in position to a second, folded-out position is achievable, as is illustrated in an exemplary manner by FIGS. 4 and 6. Defined intermediate positions according to FIG. 5 can also be assumed. FIG. 3 shows that the flexible shaft 12 is disposed in a guide duct 16 which is routed along the flexible stem 2 toward the proximal end 4. The available internal diameter of the guide duct 16 is chosen so as to be significantly larger than the external diameter of the flexible shaft 12. This enables an arrangement of the flexible shaft 12 in the guide duct 16 in which arrangement the flexible shaft 12 in portions unilaterally bears on the guide duct 16. It can be seen that the available internal diameter of the guide duct 16 is chosen so as to be larger than the external diameter of the flexible shaft 12 in order to leave sufficient freedom of movement.

An operation duct 17 which runs from the proximal end 4 to the distal end 3 and terminates at the fold-out part 7 is furthermore configured on the instrument 1. The operation duct 17 in the portion between the flexible stem 2 and the fold-out part 7 per se is configured so as to be flexible but traction-resistant and/or compression-resistant. This this enables the operation duct 17 to replicate a lateral deployment of the fold-out part 7 and for the former to simultaneously guide the fold-out part 7 when the linkage 8 is being deployed.

The linkage 8 forms a toggle lever, the knee joint 19 thereof being fixedly connected to the spindle drive 9, more specifically to the threaded counterpart 13. The spindle drive 9 thus engages on the knee joint 19 in order for the linkage 8 to be moved upright.

A first free end 20 of the toggle lever is articulated on the fold-out part, while a second free end 21 of the toggle lever is articulated on the main part.

The first free end 20 herein is configured on a first linkage arm 22 which forms a lever arm of the toggle lever. The second end 23 of the first linkage arm 22, that is opposite the knee joint 19, is guided and laterally supported in a guide groove 24 on the main part 6.

It can be seen in FIG. 3 that the toggle lever is embodied in a double manner, on account of which a particularly high lateral stability results. The double configuration in the example shown can be characterized in that, for example, the knee joints 19 define a common axis.

Figure 7:
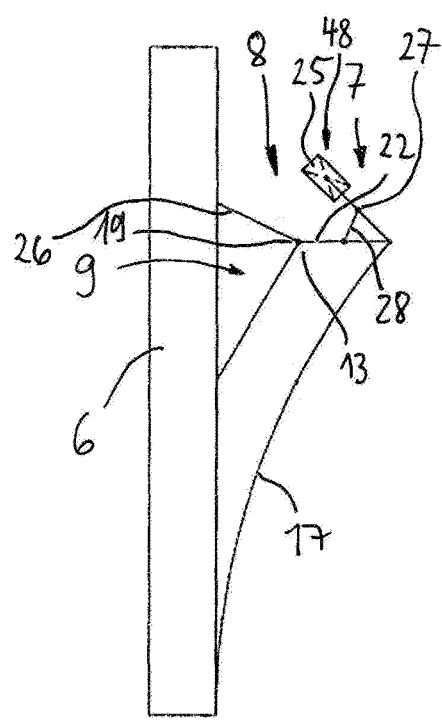
FIG. 7 shows the distal end of a further instrument according to invention, additionally having a pivotable head part.
Figure 8:
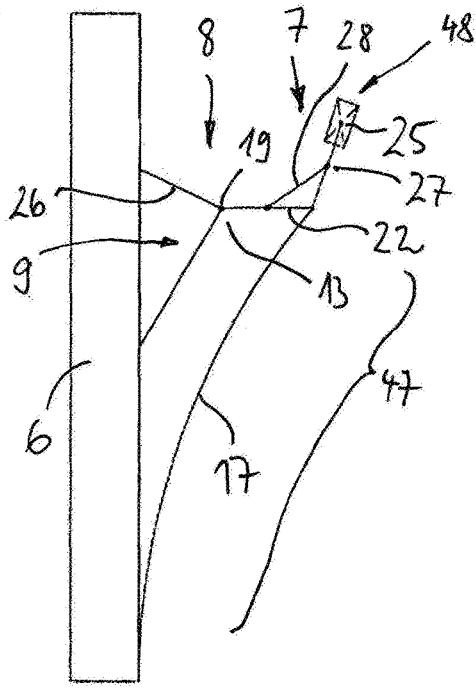
FIG. 8 shows the distal end according to FIG. 7, having an alignment of the head part that is offset in relation to the position from FIG. 7.
Figure 9:
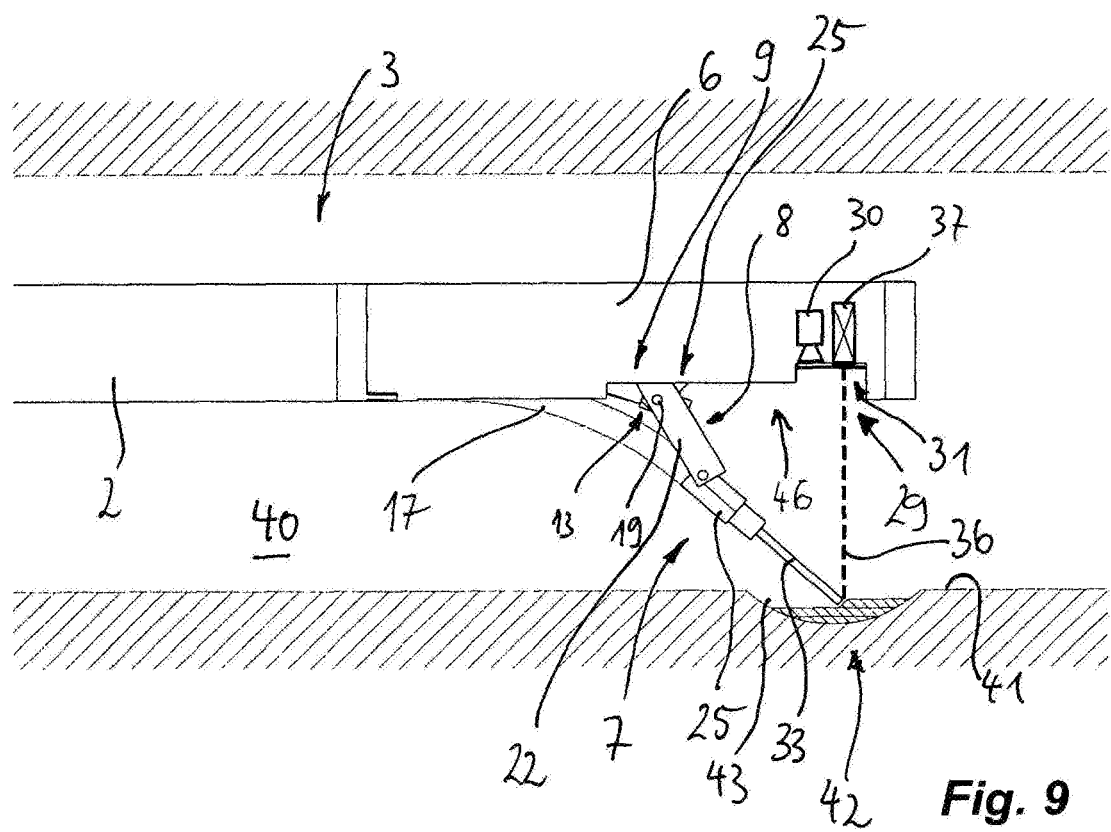
FIG. 9 shows a use according to the invention of an instrument according to the invention for repairing a component that is difficult to access.

FIGS. 7 and 8 show a variant of an instrument 1 according to the invention, in which the head part 25 has an actuation point 27 which is connected to the linkage 8 in such a manner that the head part 25 can assume dissimilar alignments.

To this end, the linkage 8 has an adjustment device 28 by way of which the head part 25 is pivotable independently of the spindle drive 9.

In the case of one variant of FIGS. 7 and 8 the actuation point 27 is connected not to the first linkage arm 22 but to the second linkage arm 26 of the toggle lever, on account of which folding in of the head part 25 is achievable in a synchronized manner with the spindle drive 9.

The main part 6 and the fold-out part 7 are in each case configured as a rigid part. A receptacle 46 into which the fold-out part 7 is placeable in the first position is configured on the main part 6.

An operation and/or observation unit 29 is likewise configured in this receptacle 46, and comprises a camera 30 and a laser light exit location 31. The camera 30 can be configured having an integrated illumination unit (not illustrated).

The operation and/or observation unit 29 is activated at least in the second position of the fold-out part 7.

A consumable material 33 from a feed installation 32 is fed to the operation duct 17 at the proximal end 4. This consumable material 33 can be a gas, fluid and/or solid material, for example a welding wire.

A monitor 34 is connected by way of an electrical or optical image conductor 35 to the operation and/or observation unit 29, in particular to the camera 30, in order for a processing of the consumable material 33 to be monitored.

The processing of the consumable material 33 is performed by way of laser light 36 which is generated by a laser generator 37 in the main part 6 or is fed by way of a laser fiber 38, and exits at the laser light exit location 31.

A machining unit 48, in particular a milling, boring and/or cutting unit, can be configured on the main part 6 and/or on the fold-out part 7 in further exemplary embodiments.

An illumination unit can additionally be configured on the main part 6, in particular as part of the operation and/or observation unit 29.

By using a camera 30 or an optical image conductor 35, the instrument is capable of being configured as a visualizing instrument, in particular as an endoscope.

It can furthermore be seen in FIG. 3 that a fiber optics 44 for an illumination (not illustrated) of the machining location is configured in the flexible stem 2.

Furthermore configured are cavities for feeding a process component, in particular for feeding process gas, during the processing of the consumable material 33.

If a camera (not illustrated) is configured on the fold-out part 7, in particular on the head part 25, instead of or in addition to the machining unit 48, stereoscopic viewing or viewing from a distance can even be carried out. If an illumination unit (not illustrated) is configured on the fold-out part 7, in particular on the head part 25, instead of or in addition to the machining unit 48 or the camera, an illumination from another angle, for example in order to avoid unfavorable shadows being cast, or an illumination at another wavelength, can be carried out.

A use according to the invention of the instrument 1 provides that the instrument 1 is fed into a cavity 40 by way of an access opening 39.

A component 41 which is difficult to access, presently in an exemplary manner an internal wall of a pipe, on which a defective location 42 is present is disposed in the cavity 40. This defective location 42 is worked so as to form a clearance 43 and is subsequently filled with the consumable material 33. It is also possible for consumable material 33 to be applied without fleshing out a clearance 43, in order for a material build-up to be carried out. In the processing of the consumable material 33, laser light 36 is used to act on the consumable material 33. This can be in the form of a welding procedure, of a soldering procedure, or else of a curing procedure for an adhesive material.

In the case of the instrument 1 it is proposed for a main part 6 and for a fold-out part 7 that is deployable from said main part 6 to be configured at the distal end 3 of a flexible stem 2, wherein the fold-out part 7 is deployable by way of a linkage 8 that is adjustable by a spindle drive 9, and wherein the spindle drive 9 from a proximal end 4 of the flexible stem 2 is drivable by way of a flexible shaft 12.

LIST OF REFERENCE SIGNS

1 Instrument
2 Flexible stem
3 Distal end
4 Proximal end
5 Handling element
6 Main part
7 Fold-out part
8 Linkage
9 Spindle drive
12 Flexible shaft
13 Threaded counterpart
15 Adjustment element
16 Guide duct
17 Operation duct
19 Knee joint
20 First free end
21 Second free end
22 First linkage arm
23 Second end
24 Guide groove
25 Head part
26 Second linkage arm
27 Actuation point
28 Adjustment device
29 Operation and/or observation unit
30 Camera
31 Laser light exit location
32 Feed installation
33 Consumable material
34 Monitor
35 Image conductor
36 Laser light
37 Laser generator
38 Laser fiber
39 Access opening
40 Cavity
41 Component
42 Defective location
43 Clearance
44 Fiber optics
45 Cavities for feeding inert gas
46 Receptacle
47 Portion
48 Machining unit

The invention claimed is:

1. An instrument (1), comprising a flexible stem (2) which has a distal end (3) and a proximal end (4), a handling element (5) disposed on the proximal end (4), a main part (6) configured on the distal end (3), a fold-out part (7) that is adjustable by way of a linkage (8) between a first position, disposed on the main part (6), and a second position which in relation to a profile direction of the stem (2) is laterally spaced apart from the main part (6), a spindle drive (9) that activates the linkage (8), the spindle drive including a threaded part (10) that is drivable by a flexible shaft (12) that extends along the stem (2), and the linkage (8) forms a toggle lever having a first linkage arm (22) and a second linkage arm (26) connected at a knee joint (19), the spindle drive (9) engages on the knee joint (19) of the toggle lever, and the second linkage arm (26) is articulated on the main part (6).

2. The instrument (1) as claimed in claim 1, wherein the flexible shaft (12) is disposed in a guide duct (16) in the stem (2).

3. The instrument (1) as claimed in claim 1, wherein the first linkage arm (22) of the linkage (8) by way of a first end (20) engages on the fold-out part, and by way of a second end (23) is displaceably guided on the main part (6).

4. The instrument (1) as claimed in claim 1, further comprising a head part (25) on the fold-out part (7), and the linkage (8) is configured to act on the head part (25).

5. The instrument (1) as claimed in claim 4, wherein a connection of the linkage (8) to the head part (25) is configured such that in the first position of the fold-out part (7) and in the second position of the fold-out part (7), the head part (25) assumes alignments that are offset.

6. The instrument (1) as claimed in claim 4, wherein one of the first linkage arm of the toggle lever is connected to the head part (25).

7. The instrument (1) as claimed in claim 1, wherein at least one of the main part (6) or the fold-out part (7) is configured as a rigid part.

8. The instrument (1) as claimed in claim 1, wherein the fold-out part (7) in the first position is received in a receptacle (46) of the main part (6).

9. The instrument (1) as claimed in claim 1, further comprising a feed installation (32) for a consumable material (33) that is conveyed in an operation duct (17) located in the stem.

10. The instrument (1) as claimed in claim 9, further comprising at least one of a laser fiber (38) or a laser light exit location (31) in the stem (2) of the main part (6) that is adapted to direct laser light on the consumable material.

11. The instrument (1) as claimed in claim 9, further comprising a machining unit for at least one of milling, boring, or cutting is configured on the fold-out part (7).

12. The instrument (1) as claimed in claim 1, wherein the instrument (1) is configured as a remote observation instrument including a camera (30) at a distal end.

13. The instrument (1) as claimed in claim 1, wherein an operation duct (17) that ends on the fold-out part (7) is configured along the stem (2), and the operation duct (17) is configured so as to be flexible at least in a portion (47) that lies between the stem (2) and the fold-out part (7).

14. The instrument (1) as claimed in claim 1, wherein a free end (20, 21) of the toggle lever engages on at least one of the main part (6) or the fold-out part (7).

15. The instrument (1) as claimed in claim 1, wherein at least one of an operation or observation unit (29) is configured on the main part (6) in a region on which the fold-out part (7) in the first position bears on the main part (6).

16. The instrument (1) as claimed in claim 1, further comprising a camera (30) configured on the main part (6).

17. A method of repairing a component using the instrument of claim 1, comprising inserting the instrument into a cavity (40) in a pipe or component, at least one of machining or repairing, an internal part of the pipe or the component by conveying a consumable material (33) by way of the instrument (1) into the cavity (40), and at least one of filling, building-up, applying a surface finish or joining at least one of a clearance (43) at a defective location (42), an internal surface, or a joint of the pipe or component (41) with the consumable material (33).

\* \* \* \* \*